United States Patent [19]
Drivon et al.

[11] Patent Number: 5,731,469
[45] Date of Patent: Mar. 24, 1998

[54] PROCESS FOR THE PREPARATION OF 3-CHLOROPROPIONIC ACID

[75] Inventors: Gilles Drivon, Saint Martin en Haut; Christophe Ruppin, Pierre-Benite, both of France

[73] Assignee: Elf Atochem S.A., Puteaux, France

[21] Appl. No.: 610,616

[22] Filed: Mar. 4, 1996

[30] Foreign Application Priority Data

Mar. 3, 1995 [FR] France .................................. 95 02484

[51] Int. Cl.$^6$ ............................................ C07C 51/00
[52] U.S. Cl. ............................................ 562/603
[58] Field of Search ............................................ 562/603

[56] References Cited

U.S. PATENT DOCUMENTS 2,571,901  10/1951  Lawlor .

FOREIGN PATENT DOCUMENTS 2 009 238   1/1970   France .
1816756     5/1993   U.S.S.R. .

*Primary Examiner*—Paul J. Killos
*Attorney, Agent, or Firm*—Millen, White, Zelano, & Branigan, P.C.

[57] ABSTRACT

A process for the preparation of 3-chloropropionic acid consists especially in simultaneously introducing hydrochloric acid gas and acrylic acid at a molar ratio of 0.7:1 to 1.3:1 into a sediment consisting of 3-chloropropionic acid optionally diluted with water or with an aqueous hydrochloric acid solution.

19 Claims, No Drawings

PROCESS FOR THE PREPARATION OF 3-CHLOROPROPIONIC ACID

BACKGROUND OF THE INVENTION

The present invention relates to a process for the preparation of 3-chloropropionic acid by hydrochlorination of acrylic acid.

3-chloropropionic acid is an important intermediate in the manufacture of biocides, colorants, pharmaceutical products, cosmetic products and additives for plastics.

Russian Patent SU 438639 describes a process which consists in reacting acrylic acid with an aqueous solution of hydrochloric acid in the presence of a quaternary ammonium salt.

The reaction mixture is kept at a temperature close to room temperature, with vigorous stirring, for several hours, and then the unreacted hydrochloric acid and water are removed by distillation under reduced pressure.

After azeotropic drying, 3-chloropropionic acid is obtained with a yield of 87%.

American Patent U.S. Pat. No. 2,759,018 describes a process for the preparation of 3-chloropropionic acid by reacting an aqueous solution of acrylic acid with hydrochloric acid gas at a temperature of less than 60° C. The acrylic acid concentration by weight of the aqueous acrylic acid solution is preferably of between 10% and 30%.

The operating conditions used in the two abovementioned processes are such that the reaction for the hydrochlorination of acrylic acid is very slow and the 3-chloropropionic acid yields are very low. In addition, at the end of the operation, the necessary separation of water as well as of substantial quantities of hydrochloric acid and/or of quaternary ammonium salt are expensive and crippling operations for the economics Of an industrial process.

German Patent DE 2,555,043 describes a process for the manufacture of 3-chloropropionic acid which consists in reacting, at a pressure ranging from 1.5 bar to 5 bar, acrylic acid with hydrochloric acid gas in an acrylic acid/hydrochloric acid mol ratio ranging from 1 to 1.5, at a temperature of between 40° C. and 80° C.

Although this process leads to a high productivity combined with good selectivity, it has the major disadvantage of taking place under hydrochloric acid gas pressure, which requires the use of a very specific and expensive equipment.

SUMMARY OF THE INVENTION

A semicontinuous process has now been found for the preparation of 3-chloropropionic acid by hydrochlorination of acrylic acid, characterized in that hydrochloric acid gas and acrylic acid are simultaneously introduced into a sediment, essentially consisting of:

70% to 100% by weight of 3-chloropropionic acid and,
0% to 30% by weight of water or of an aqueous solution of hydrochloric acid, and then the introduction of the hydrochloric acid gas is optionally continued.

According to the present invention, the hydrochloric acid and the acrylic acid are simultaneously introduced in a hydrochloric acid/acrylic acid mol ratio of between 0.70 and 1.30 and, preferably, in a mol ratio of between 0.8 and 1.15.

According to the present invention, the sediment consists of pure 3-chloropropionic acid, or of 3-chloropropionic acid diluted with a quantity of water by weight preferably of between 5% and 20%, or alternatively of 3-chloropropionic acid diluted with a quantity of an aqueous hydrochloric acid solution by weight preferably of between 5% and 25%.

The hydrochloric acid concentration by weight of the aqueous hydrochloric acid solutions which can be used according to the present invention is at least equal to 20%, and preferably is between 22% and 37%.

The sediment is heated beforehand to a temperature at least equal to 30° C. and, preferably, to a temperature of between 40° C. and 60° C. During the simultaneous introduction of the hydrochloric acid gas and the acrylic acid, during the optional continuation of the introduction of HCl gas and after the end of the introduction of the reagents, the temperature of the reaction medium is advantageously maintained between 40° C. and 60° C.

According to the present invention, the procedure is preferably carried out at atmospheric pressure.

According to the present invention, the process is carried out in a vitrified steel or a glass reactor provided with stirring, means of heating, of introducing gas and/or liquid, of measuring temperature, a distillation column optionally linked to a system for trapping HCl.

The stirring of the reaction medium can be carried out by any means which provides a good gas/liquid contact.

The acrylic acid which can be used according to the present invention has a purity at least equal to 95% and is generally stabilized by means of small quantities of alkyl esters of hydroquinone. The acrylic acid may also contain inert impurities in very small quantities, such as acetic acid and propionic acid.

According to the present invention, the sediment represents at most 30% by volume of the reactor used to carry out the process. The hydrogen chloride can be introduced by means of a tube immersed in the said sediment. It can also be introduced by any appropriate device through the bottom of the reactor.

According to the present invention, the quantities of hydrochloric acid gas and acrylic acid simultaneously introduced are similar to the stoichiometric quantities of the reaction:

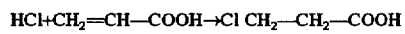

$$HCl + CH_2=CH-COOH \rightarrow Cl\ CH_2-CH_2-COOH$$

These quantities are such that the hydrochloric acid gas/acrylic acid mol ratio is between 0.70 and 1.30 and preferably between 0.80 and 1.15.

In the event that the procedure is carried out with a slight excess of hydrochloric acid relative to the acrylic acid, the concentration of acrylic acid in the reaction medium is minimized.

However, this manner of proceeding can cause small losses of hydrochloric acid in the gas ports.

In the case where the procedure is carried out with a slight shortage of hydrochloric acid relative to the acrylic acid, the possible losses of hydrochloric acid in the gas ports are minimized but the residual acrylic acid concentration in the reaction medium is higher.

According to the present invention, the introduction of hydrogen chloride following the simultaneous introduction of HCl gas and acrylic acid can be maintained for a sufficient period so as to obtain especially a residual acrylic acid quantity by weight of less than 2% and preferably of less than or equal to 1%.

This period of introduction of hydrochloric acid gas can vary to a large extent and is a function, especially of the quantities of hydrochloric acid gas simultaneously introduced with the acrylic acid, the quantities of water contained in the sediment and the efficiency of the gas/liquid contact achieved by the system for stirring the reaction medium.

It is at most equal to 10 hours and, preferably, of between 1 and 5 hours.

This introduction of hydrochloric acid gas, following the simultaneous introduction of HCl gas and acrylic acid, can be suppressed in the case where the sediment consists of 3-chloropropionic acid diluted with an aqueous solution of hydrochloric acid.

The progress of the reaction can be monitored either by determining the 3-chloropropionic acid formed by means of gas chromatography analysis and/or proton nuclear magnetic resonance analysis, or by measuring the quantity of hydrochloric acid by potentiometric assay.

According to the present invention, in the case where the procedure is carried out with a sediment solely consisting of 3-chloropropionic acid and when the introduction of hydrochloric acid gas following the simultaneous introduction of HCl gas and acrylic acid is complete, the unreacted dissolved hydrochloric acid is removed either by degassing by means of an inert gas such as nitrogen, or by placing under reduced pressure.

In the case where the procedure is carried out using a sediment containing 3-chloropropionic acid diluted with water or with an aqueous hydrochloric acid solution, the aqueous and/or dissolved hydrochloric acid is removed by azeotropic topping under reduced pressure.

In all cases, the 3-chloropropionic acid is recovered with a practically quantitative yield relative to the acrylic acid used and a 3-chloropropionic acid titre at least equal to 94% is obtained.

The 3-chloropropionic acid thus obtained may then be directly used as intermediate reagent in the synthesis of pharmaceutical products.

It may also be diluted with water so as to obtain liquid aqueous solutions which can be easily transported without any risk of crystallization.

The process according to the invention has the advantage of being carried out at atmospheric pressure not requiring any specific apparatus.

According to the present invention, a rapid reaction kinetics and a practically quantitative yield of 3-chloropropionic acid relative to the acrylic acid are also obtained.

The process according to the present invention also has the advantage of leading to a minimum loss of hydrochloric acid gas and to a 3-chloropropionic acid having a residual acrylic acid content by weight of less than 2%.

The following examples illustrate the invention.

EXAMPLE 1

217 g of 3-chloropropionic acid stabilized with 200 ppm of methyl ester of hydroquinone are charged into a 1 l glass reactor.

The mixture is heated to around 45° C. and then there are simultaneously introduced over 5 h:
 360 g of acrylic acid at a flow rate of 1 mol/h
 237 g of anhydrous HCl at a flow rate of 1.3 mol/h
while the temperature is maintained at a value of about 45° C.

When all the acrylic acid has been introduced, the acrylic acid concentration in the reaction medium is equal to 5.8%, the supply of HCl is then maintained at a flow rate of 0.5 mol/h until the theoretical quantity of HCl is absorbed, that is to say for 2 hours.

The progress of the reaction is monitored by potentiometric assay of the HCl absorbed.

The reaction medium is then maintained for 1 h at about 45° C. and then degassed for 1 h by a slight bubbling of nitrogen.

756 g of a crude product having an NMR purity >94%, containing less than 1% residual acrylic acid and less than 0.5% hydrochloric acid, are obtained.

This product is either stored as it is, or diluted with 185 g of distilled water so as to obtain an aqueous solution at a 3-chloropropionic acid concentration of 80%, which solution does not crystallize at a temperature greater than 10° C.

EXAMPLES 2, 3 AND 4

The procedure is carried out in the same equipment as in Example 1, using in each example a sediment consisting of 217 g of pure 3-chloropropionic acid.

The single table below presents the reaction parameters as well as the acrylic acid concentrations in the reaction media.

In this table, the following meanings are used:

$T(°C.)$ temperatures for heating the sediment and the reaction medium during stages I and II, STAGE I stage for simultaneous introduction into the sediment of acrylic acid and hydrochloric acid gas (HCl gas), STAGE II introduction of HCl gas, $D_{INT}$ period of introduction in hours, $[AA]_I$ acrylic acid concentration by weight in the reaction medium after stage I, After stage II, the reaction medium is maintained for 1 hour at about 45° C. and then degassed for 1 hour by a slight bubbling of nitrogen.

3-chloropropionic acid is thus obtained whose residual acrylic acid concentration by weight is designated by $[AA]_{II}$ in the single table.

SINGLE TABLE

| | | STAGE I | | | STAGE II | | |
|---|---|---|---|---|---|---|---|
| | | | Flow rate | | | HCl gas | |
| | | | (mol/h) | | | Flow | |
| Example | T (°C.) | $D_{INT}$ (h) | Acrylic acid | HCl gas | $[AA]_I$ (%) | $D_{INT}$ (h) | rate (mol/h) | $[AA]_{II}$ (%) |
| 2 | 45–50 | 5 | 1 | 1.15 | 10.7 | 3 | 0.5 | ≤1 |
| 3 | 45–50 | 5 | 1 | 1 | 15.8 | 4 | 0.5 | ≤1 |
| 4 | 45–50 | 5 | 1 | 0.8 | 22.5 | 5 | 0.5 | ≤1 |

EXAMPLE 5

The procedure is carried out in the same equipment as in Example 1.

217 g of pure 3-chloropropionic acid and 19 g of water which corresponds to a sediment containing 8% by weight of water is initially charged, and then hydrochloric acid gas and acrylic acid are simultaneously introduced over 5 hours, at a temperature of 45° C.–50° C., at the same flow rate of 1 mol/hour.

At this stage, the acrylic acid concentration by weight in the reaction medium is 5.2%.

The addition of HCl gas at a flow rate of 0.5 mol/hour is then continued for 2 hours.

The reaction medium is then maintained for one hour at about 45° C. and then topped under reduced pressure in order to remove aqueous HCl.

752 g of 3-chloropropionic acid containing less than 1% residual acrylic acid are obtained.

EXAMPLE 6

The procedure is carried out in the same equipment as in Example 1.

217 g of pure 3-chloropropionic acid and 84 g of a 33% aqueous solution of hydrochloric acid are initially charged.

There are then introduced, simultaneously and for 5 hours, at a temperature of between 45° C. and 50° C., hydrochloric acid gas at a flow rate of 1.1 mol/hour and acrylic acid at a flow rate of 1 mol/hour.

The reaction medium is then maintained for 1 hour at about 45° C. and then azeotropic topping is carried out under reduced pressure in order to remove the aqueous hydrochloric acid.

745 g of 3-chloropropionic acid containing less than 1% by weight of residual acrylic acid are recovered.

The aqueous hydrochloric acid can then be reused to dilute the 3-chloropropionic acid of the sediment of a subsequent operation.

The preceding examples can be repeated with similar success by substituting the generically or specifically described reactants and/or operating conditions of this invention for those used in the preceding examples.

The entire disclosure of all applications, patents and publications, cited above and below, and of corresponding French application 95/02484, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. In a process for the preparation of 3-chloropropionic acid by hydrochlorination of acrylic acid, the improvement comprising simultaneously introducing hydrochloric acid gas and acrylic acid into a sediment previously heated to at least 30° C., said sediment consisting essentially of:

70% to 100% by weight of 3-chloropropionic acid and,
   0% to 30% by weight of water or of an aqueous solution of hydrochloric acid of a concentration of 20–37% by weight; and then optionally continuing the introduction of the hydrochloric acid gas.

2. A process according to claim 1, wherein the sediment consists essentially of anhydrous 3-chloropropionic acid.

3. A process according to claim 1, wherein the sediment consists essentially of 3-chloropropionic acid diluted with a quantity of water by weight of between 5% and 20%.

4. A process according to claim 1, wherein the sediment consists essentially of 3-chloropropionic acid diluted with a quantity of said aqueous hydrochloric acid solution by weight of between 5% and 25%.

5. A process according to claim 1, wherein the hydrochloric acid gas and acrylic acid are simultaneously introduced in a HCl gas/acrylic acid mol ratio of between 0.70 and 1.30.

6. A process according to claim 2, wherein the hydrochloric acid gas and acrylic acid are simultaneously introduced in a HCl gas/acrylic acid mol ratio of between 0.70 and 1.30.

7. A process according to claim 3, wherein the hydrochloric acid gas and acrylic acid are simultaneously introduced in a HCl gas/acrylic acid mol ratio of between 0.70 and 1.30.

8. A process according to claim 4, wherein the hydrochloric acid gas and acrylic acid are simultaneously introduced in a HCl gas/acrylic acid mol ratio of between 0.70 and 1.30.

9. A process according to claim 5, wherein the HCl gas/acrylic acid mol ratio is between 0.80 and 1.15.

10. A process according to claim 6, wherein the HCl gas/acrylic acid mol ratio is between 0.80 and 1.15.

11. A process according to claim 7, wherein the HCl gas/acrylic acid mol ratio is between 0.80 and 1.15.

12. A process according to claim 8, wherein the HCl gas/acrylic acid mol ratio is between 0.80 and 1.15.

13. A process according to claim 12, wherein the sediment is heated beforehand to a temperature of between 40° and 60° C., and maintained at said temperature during the hydrochlorination.

14. A process according to claim 12, wherein the sediment is heated beforehand to a temperature of between 45° and 50° C. and maintained at said temperature during the hydrochlorination.

15. A process according to claim 12, wherein the sediment is heated beforehand to a temperature of between 40° and 60° C., and maintained at that temperature during the hydrochlorination.

16. A process according to claim 1, wherein after the simultaneous introduction of hydrochloric acid gas and acrylic acid, the introduction of hydrochloric acid is continued so as to yield a residual concentration of acrylic acid in the resultant product of less than 2% by weight.

17. A process according to claim 16, wherein the continued introduction of hydrochloric gas occurs for 1 to 10 hours and the residual acrylic acid is less than 1% by weight.

18. A process according to claim 1, conducted in a reactor wherein the sediment represents at most 30% by volume of the reactor.

19. A process according to claim 1, wherein the hydrochlorination is conducted in a system consisting essentially of hydrochloric acid gas, acrylic acid, 3-chloropropionic acid and optionally water or an aqueous solution of hydrochloric acid.

* * * * *